(12) United States Patent
Pezacki et al.

(10) Patent No.: US 10,745,735 B2
(45) Date of Patent: Aug. 18, 2020

(54) DETECTION, ISOLATION AND IDENTIFICATION OF MICROORGANISMS

(71) Applicant: NATIONAL RESEARCH COUNCIL OF CANADA, Ottawa (CA)

(72) Inventors: John Pezacki, Ottawa (CA); Allison Sherratt, Ottawa (CA); Yanouchka Rouleau, Gatineau (CA)

( * ) Notice: Subject to any disclaimer, the term of this patent is extended or adjusted under 35 U.S.C. 154(b) by 502 days.

(21) Appl. No.: 15/037,862

(22) PCT Filed: Nov. 25, 2014

(86) PCT No.: PCT/CA2014/000846
§ 371 (c)(1),
(2) Date: May 19, 2016

(87) PCT Pub. No.: WO2015/074141
PCT Pub. Date: May 28, 2015

(65) Prior Publication Data
US 2016/0289730 A1    Oct. 6, 2016

Related U.S. Application Data

(60) Provisional application No. 61/907,570, filed on Nov. 22, 2013.

(51) Int. Cl.
| | |
|---|---|
| C12Q 1/00 | (2006.01) |
| G01N 33/53 | (2006.01) |
| G01N 33/569 | (2006.01) |
| C12Q 1/10 | (2006.01) |
| C12Q 1/04 | (2006.01) |
| C12N 1/20 | (2006.01) |

(52) U.S. Cl.
CPC ............. *C12Q 1/10* (2013.01); *C12N 1/20* (2013.01); *C12Q 1/04* (2013.01); *G01N 33/56916* (2013.01)

(58) Field of Classification Search
CPC ............ C12Q 1/10; C12Q 1/04; G01N 33/58
USPC .............................................. 435/4, 7.1, 7.2
See application file for complete search history.

(56) References Cited

U.S. PATENT DOCUMENTS

| | | | |
|---|---|---|---|
| 6,344,332 | B1 | 2/2002 | Thacker |
| 7,910,319 | B2 | 3/2011 | Wong et al. |
| 2004/0241848 | A1 | 12/2004 | Hong |
| 2008/0267878 | A1 | 10/2008 | Robillard et al. |
| 2009/0214439 | A1 | 8/2009 | Kumar et al. |
| 2010/0189660 | A1 | 7/2010 | Hannoush |
| 2010/0203647 | A1 | 8/2010 | Hang et al. |
| 2010/0247433 | A1 | 9/2010 | Tirrell |
| 2011/0064667 | A1 | 3/2011 | Robillard et al. |

FOREIGN PATENT DOCUMENTS

| | | |
|---|---|---|
| JP | 07-023794 | 1/1995 |
| WO | 1995/012687 | 5/1995 |
| WO | 2011/021008 | 2/2011 |
| WO | 2011/028494 | 3/2011 |

OTHER PUBLICATIONS

Allen JJ, Lazerwith SE, Shokat KM. (2005) Bio-orthogonal Affinity Purification of Direct Kinase Substrates. J Am Chem Soc. 127(15), 5288-5289.
Beatty KE, Xie F, Wang Q, Tirrell DA. (2005) Selective Dye-Labeling of Newly Synthesized Proteins in Bacterial Cells. J. Am. Chem. Soc. 127, 14150-14151.
Beatty KE, Fisk JD, Smart BP, Lu YY, Szychowski J, Hangauer MJ, Baskin JM, Bertozzi CR, Tirrell DA. (2010) Live-cell Imaging of Cellular Proteins by a Strain-Promoted AzideAlkyne Cycloaddition. Chembiochem. 11, 2092-2095.
Besanceney-Webler C, Jiang H, Wang W, Baughn AD, Peng W. (2011) Bioorganic & Medicinal Chemistry Letters. doi: 10.1016/j.bmcl.2011.05.038.
Dieterich DC, Lee JJ, Link AJ, Graumann J, Tirrell DA, Schuman EM. (2007) Labeling, detection and identification of newly synthesized proteomes with bioorthogonal noncanonical amino-acid tagging. Nature Protocols. 2(3), 532-540.
Dukan S, Dumont A, Awwad M, Malleron A, Vauzeilles B. (2013) A method for specifically detecting living bacteria. European Patent Publication EP 2617833 published Jul. 24, 2013.
Dumont A, Malleron A, Awwad M, Dukan S, Vauzeilles B. (2012) Click-mediated labeling of bacterial membranes through metabolic modification of the lipopdlysaccharide inner core. Angew Chem Int Ed Engl. 51(13), 3143-3146.
Fetzer I, Jehmlich N, Vogt C, Richnow H-H, Seifert D, Harms H, Bergen M van, Schmidt F. (2010) Calculation of partial isotope incorporation into peptides measured by mass spectrometry. BMC Research Notes. 3, 178 (9 pages).
Hsu TL, Hanson SR, Kishikawa K, Wang SK, Sawa M, Wong CH. (2007) Alkynyl sugar analogs for the labeling and visualization of glycoconjugates in cells. Proc. Natl. Acad. Sci. U.S.A. 104, 2614-2619.

(Continued)

*Primary Examiner* — Rodney P Swartz
(74) *Attorney, Agent, or Firm* — Jessica Smith

(57) ABSTRACT

A method of selectively identifying live microorganisms in a sample involves contacting a sample suspected of containing a live microorganism of interest with a biomolecular precursor labeled with a reactive chemical label. The live microorganism of interest is grown under conditions that promote selective growth of the microorganism to permit the microorganism to utilize the labeled biomolecular precursor to synthesize labeled biomolecules on a cell surface of the live microorganism. Labeled live microorganisms are contacted with a reporter and/or capture element bearing a functional group that reacts with the reactive chemical label. The labeled live microorganism is analyzed to identify it. The method can specifically isolate live microorganisms from dead ones thereby reducing the possibility of false identification of contaminating microorganisms and is able to detect specific strains using tailored metabolites that are specific for a given microorganism. The present method is considerably faster than currently used cell culture-based methods.

19 Claims, 11 Drawing Sheets

(56) References Cited

OTHER PUBLICATIONS

Kennedy DC, McKay CS, Legault MC, Danielson DC, Blake JA, Pegoraro AF, Stolow A, Mester Z, Pezacki JP. (2011) Cellular consequences of copper complexes used to catalyze bioorthogonal click reactions. J. Am. Chem. Soc. 133, 17993-18001.

Kulla H. (1994) Device and Method for the Detection of Microorganisms which Produce Low-Molecular-Weight Metabolites. U.S. Pat. No. 5,348,884 issued Sep. 20, 1994.

Lim RKV, Lin Q. (2010) Bioorthogonal Chemistry: Recent Progress and Future Directions. Chem Commun (Camb). 46 (10), 1589-1600.

Link AJ, Tirrell DA. (2003) Cell Surface Labeling of *Escherichia coli* via Copper(I)Catalyzed [3+2] Cycloaddition. J. Am. Chem. Soc. 125, 11164-11165.

Link AJ, Vink MK, Tirrell DA. (2004) Presentation and Detection of Azide Functionality in Bacterial Cell Surface Proteins. J. Am. Chem. Soc. 126, 10598-10602.

Ngo JT, Champion JA, Mandavi A, Tanrikulu IC, Beatty KE, Connor RE, Yoo TH, Dieterich DC, Schuman EM, Tirrell JA. (2009) Cell-selective metabolic labeling of proteins. Nat. Chem. Biol. 5, 715-717.

Ngo JT, Tirrell DA. (2011) Noncanonical amino acids in the interrogation of cellular protein synthesis. Acc Chem Res. 44, 677-685.

Sadamoto R, Matsubayashi T, Shimizu M, Ueda T, Koshida S, Koda T, Nishimura S. (2008) Bacterial Surface Engineering Utilizing Glucosamine Phosphate Derivatives as Cell Wall Precursor Surrogates. Chemistry. 14(33), 10192-10195.

Van Duyne GD, Standaert RF, Karplus PA, Schreiber SL, Clardy J. (1993) Atomic structures of the human immunophilin FKBP-12 complexes with FK506 and rapamycin. J Mo/ Biol. 229(1), 105-124.

Yang Y-Y, Ascano JM, Hang HC. (2010a) Bioorthogonal Chemical Reporters for Monitoring Protein Acetylation. J Am Chem Soc. 132(11), 3640-3641.

Yang Y-Y, Grammel M, Raghavan AS, Charron G, Hang HC. (2010b) Comparative Analysis of Cleavable Azobenzene-Based Affinity Tags for Bioorthogonal Chemical Proteomics. Chemistry & Biology. 17, 1212-1222.

Yang Y-Y, Grammel M, Hang HC. (2011) Identification of lysine acetyltransferase p300 substrates using 4- pentynoylcoenzyme A and bioorthogonal proteomics. Bioorganic & Medicinal Chemistry Letters. doi: 10.1016/j. bmcl.2011.05.060.

Zheng Q, Saha S, Lee LA, Barnhill H, Oxsher J, Dreher T, Wang Q. (2011) Chemoselective Modification of Turnip Yellow Mosaic Virus by Cu(I) Catalyzed AzideAlkyne 1,3-Dipolar Cycloaddition Reaction and Its Application in Cell Binding. Bioconjug. Chem. 22(1), 58-66.

Hatzenpichler, R. et al., "In situ visulization of newly synthesized proteins in environmental microbes using amino acid tagging and click chemistry" Env. Micro. Apr. 2, 2014, V. 16(8), p. 2568-90.

Sherratt, A.R. et al. "Copper-catalysed cycloaddition reactions of nitrones and alkynes for biorthogonal labelling of living cells" RSC Advances, Sep. 17, 2014, v. 4, p. 46966-69.

Ouellette, S.P. et al. "Chlamydia Species-Dependant Differences in the Growth Requirements for Lysosomes" Plos ONE. Mar. 8, 2011, V. 6(3), e16783, p. 1-16.

Byrne, B. et al. Antibody-Based Sensors: Principles, Problems and Potential for Detection of Pathogens and Associated Toxins, Sensors. Jun. 5, 2009, V. 9, p. 4407-4445.

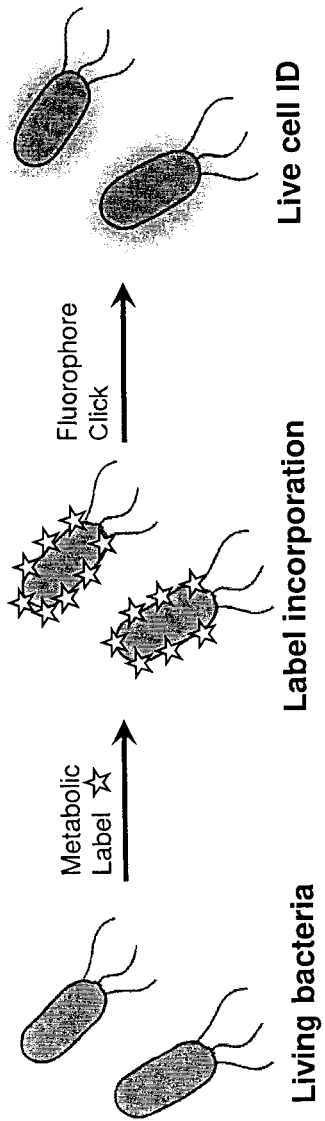
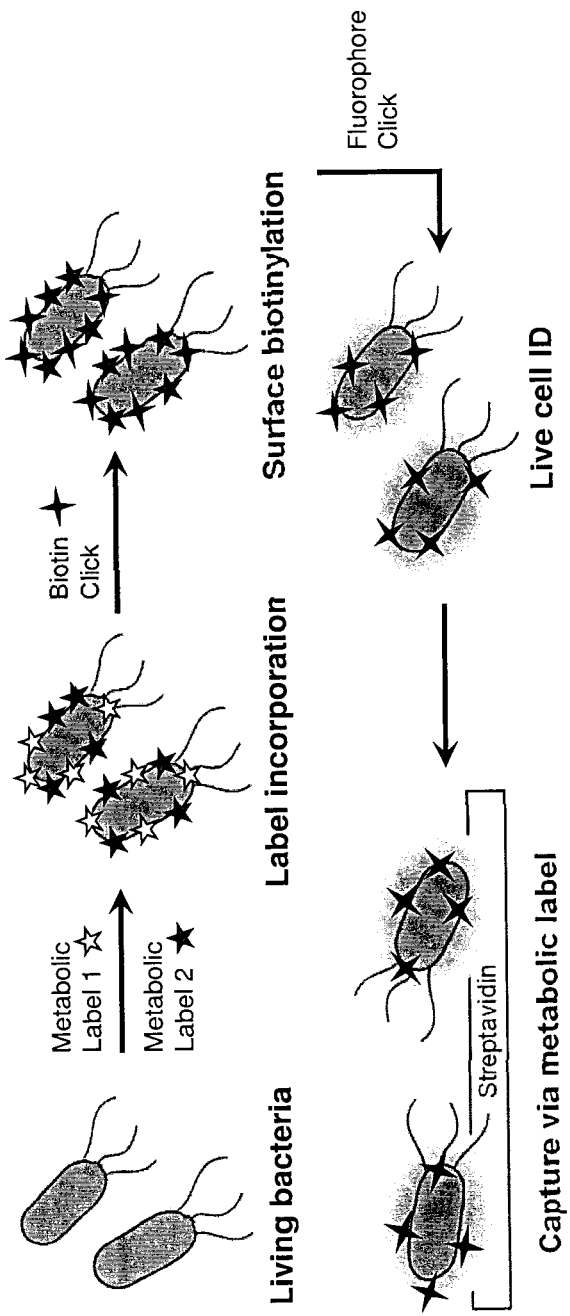
Fig. 1A
Fig. 1B

DETECTION, ISOLATION AND IDENTIFICATION OF MICROORGANISMS

This application is a national phase entry of International Patent Application No. PCT/CA2014/000856 filed Nov. 25, 2014 and claims the benefit of United States Provisional Patent Application Serial No. 61/907,570 filed Nov. 22, 2013, the entire contents of both of which are herein incorporated by reference.

FIELD OF THE INVENTION

The present invention relates to methods of identifying microorganisms in a sample.

BACKGROUND OF THE INVENTION

Recent high profile outbreaks of verotoxigenic *Escherichia coli* (VTEC) and Listeriosis have brought food and water safety to the forefront of public concern. These outbreaks have highlighted the urgent need for rapid, sensitive and field deployable methods for pathogen detection and characterization in foodstuffs.

The detection and identification of bacterial contaminants in foodstuffs is currently an area of intense research and development. Currently, regulatory agencies make decisions regarding the removal of contaminated products from the supply chain using culture-based methods that are labor intensive and time consuming (5-9 days to detect bacterial pathogens). Most emerging technologies in this area focus on the specific detection and identification of bacterial strains using genetic material, but require large quantities of DNA/RNA and are unable to identify live bacteria from dead ones that are found abundantly throughout treated food samples. There is currently no rapid method for assaying whether a pathogenic material that might test positive in a PCR or antibody-based IVD test is alive or dead. This is required for regulators to take legal action and for suppliers to prevent legal action.

Metabolic labeling of microorganisms and bio-orthogonal click chemistry for the purpose of detection or glycoproteomic analysis is known in the art (e.g. Besanceney-Webler-2011; Yang 2010a; Yang 2010b; Yang 2011; Dumont 2012). However, such techniques often rely on the destruction of cells for further analysis and are therefore unsuitable for specific identification of live microorganisms. Methods of identifying bacteria are known (e.g. Akihiko 1995; Pollard 1995; Kulla 1994), which involve incorporating various radioactive or non-radioactive isotopes into bacterial cells followed by detection of the isotope. These methods are usually slow and tedious and often require destruction of cells to perform the analysis. Further, detection methods for bacteria employing the detection of metabolized substrates (e.g. Thacker 2002; Dukan 2013) have been used, but these methods suffer from a variety of limitations including the inability to separate live microorganisms from the sample leading to interferences and inaccuracies in the identification of microorganisms in the sample.

There remains a need for improved methods for detecting live microorganisms that provide faster identification, using less material and in a manner that can maintain the integrity of live bacteria for further identification analysis.

SUMMARY OF THE INVENTION

In one aspect of the invention there is provided a method of selectively identifying live microorganisms in a sample comprising: contacting a sample suspected of containing a live microorganism of interest with a biomolecular precursor labeled with a reactive chemical label; growing the live microorganism of interest under conditions that promote selective growth of the microorganism to permit the microorganism to utilize the labeled biomolecular precursor to synthesize labeled biomolecules on a cell surface of the live microorganism to produce a labeled live microorganism; contacting the labeled live microorganism with a reporter and/or capture element bearing a functional group that reacts with the reactive chemical label to permit identification of the live microorganism; and, analyzing the labeled live microorganism to identify it.

In another aspect of the invention there is provided a kit comprising a biomolecular precursor labeled with a reactive chemical label, a reporter and/or capture element bearing a functional group that reacts with the reactive chemical label, a vessel for growing the microorganism of interest and conducting a reaction between the labeled biomolecular precursor and the functionalized reporter and/or capture element, growth medium for a microorganism of interest, nutritional factors necessary for growing the microorganism of interest, and instructions for using the kit to identify the microorganism of interest.

Using bio-orthogonal chemical reactions, biomolecules of microorganisms can be labeled with reactive chemical labels that are incorporated metabolically using labeled biomolecular precursors to which the microorganisms are exposed. Biomolecular precursors include, for example, components for building lipids, carbohydrates, proteins or polynucleotides. Such components may comprise basic building blocks for constructing biomolecules, for example, amino acids, nucleic acids, sugars or fatty acids, or may comprise larger compounds that are metabolically incorporated, for example, intact peptides, complex carbohydrates, complex lipids or polynucleotides. One type of biomolecular precursor may be utilized, or two or more different biomolecular precursors labeled with a reactive chemical label may be utilized. Preferably, the biomolecular precursor comprises an amino acid (e.g. methionine or methionine analogue), a sugar (e.g. 3-deoxy-D-manno-oct-2-ulosonic acid (KDO)) or a mixture thereof. Preferably, the biomolecule targeted with the biomolecular precursor is located on the surface of the microorganism.

The biomolecular precursor may be specifically targeted to a particular microorganism. Certain biomolecular precursors are only metabolically incorporated by specific species of microorganisms. By using such a specific biomolecular precursor, it is possible to tailor the method to only detect a single species, or small groups of species, of interest. This leads to a more specific assay yielding more rapid identification of whether a sample contains the specific microorganism of interest. For example, the *Bacteroidales* species expresses a fucose salvage pathway which allows it to incorporate exogenous fucose into surface glycoproteins (Besanceney-Webler-2011); a pathway that is quite rare among bacteria.

Reactive chemical labels are incorporated metabolically into the microorganism. For this reason, the reactive chemical label should be non-toxic to the microorganism to preserve the viability of the microorganism for further analysis. Preferably, the reactive label does not significantly slow the growth of the microorganism of interest. Preferably, the reactive label is metabolically incorporated into the microorganism within days (e.g. within 3 days), more preferably within hours (e.g. within 12 hours) even more preferably within minutes (e.g. within 60 minutes). Preferably, the reactive chemical label is metabolically incorporated in less than eight hours, more preferably less than one hour, for example less than 30 minutes.

In one embodiment, the biomolecular precursor containing the reactive chemical label may be an unnatural amino acid such as homopropargylglycine (HPG) or azidohomoalanine (AHA). Methionine analogues such as HPG and AHA are substrates for natural translational machinery (Ngo 2011), and are incorporated into expressed protein after treatment to inhibit methionine biosynthesis. Feedback inhibition of methionine biosynthesis through supplementation with lysine, threonine, phenylalanine, isoleucine, valine and leucine forces bacteria to acquire methionine (or methionine analogues) from the media regardless of the capacity to synthesize methionine on their own, as previously applied to selenomethionine labeling in X-ray crystallography (Van Duyne 1993) for structural biology purposes only. In this embodiment, incorporation of HPG into bacterial surface proteins was detected after thirty minutes of contact between the microorganism and methionine analogue. Furthermore, it is possible to capture living bacteria via an incorporated unnatural amino acid, while dead and therefore unlabeled bacteria are not captured.

In another embodiment, the biomolecular precursor containing the reactive chemical label may be a functionalized sugar such as KDO-alkyne, KDO-azide or KDO-nitrone. Such sugar analogues are directed to the inner core of the lipopolysaccharides found in gram negative bacterial outer membranes (Dumont 2012). Supplementation of KDO or KDO analogues in metabolic labeling medium has been observed to enhance microorganism growth, as opposed to inhibit growth. Furthermore, in this embodiment metabolic labeling has been observed within five hours of contact between the microorganism and KDO analogue. Although this labeling method provides an additional technique to identify living gram negative bacteria, it can be used for analysis purposes only as capture is not possible.

Reactive chemical labels are able to react with an appropriate functional group of a reporter/capture element. Reactive chemical labels and the functional groups on the reporter/capture elements are paired chemical species chosen for their ability to react with each other in bio-orthogonal reactions. The bio-orthogonal reaction between the reactive chemical label and the functional group forms the basis of the ability to identify live microorganisms of interest from dead ones or ones that do not incorporate the reactive chemical label, since only the live microorganisms will have incorporated the reactive chemical label metabolically. Upon reaction between the reactive chemical label and the functional group, microorganisms having the reactive chemical label incorporated therein may be identified in and/or captured from a sample that is filled with other material originally present in or are generated or used during treatment of the sample, including dead microorganisms and other microorganisms not able to incorporate the reactive chemical label.

Table 1 provides an exemplary list of paired chemical species, one of which may be the reactive chemical label and the other of which may be the functional group on the reporter/capture element, or vice versa. Of particular note is the alkyne/azide pair.

TABLE 1

| Chemical Species 1 | Chemical Species 2 |
| --- | --- |
| Alkyne | Azide |
| Nitrone | Alkyne |
| Azide | Phosphine |

TABLE 1-continued

| Chemical Species 1 | Chemical Species 2 |
| --- | --- |
| Azide | Strained alkyne |
| Strained Alkene | Tetrazine |
| Aldehyde or Ketone | Aminooxy or Hydrazide |
| Thiol | Alkene |
| Alkene | Diaryl tetrazole |

Reporter/capture elements may be molecules that bear the bio-orthogonal reactive functional group. Reporter/capture elements may possess a property, for example fluorescence, that may be detected using any suitable technique, for example, fluorescence assays or microscopy. Reporter/capture elements may comprise one or more molecular species that contribute to reporting and/or capturing, for example fluorophores, biotin, microorganism-specific antibodies, streptavidin and the like. Reporter/capture elements may be free in solution or suspension, or may be supported on or bound to a surface of a physical substrate. Physical substrates may comprise, for example, beads, particles or microfluidic devices. Magnetic beads or particles, especially magnetic nanoparticles or magnetic micron beads, are of particular note.

In a preferred embodiment, the sample may be separated from the labeled live microorganism before analyzing the labeled live microorganism to separate intact cells of the labeled live microorganism from unlabeled microorganisms in the sample. Separation of the live microorganisms from the rest of the sample, including dead microorganisms, may be achieved physically by any suitable method depending on the nature of the capture element used. For example, in microfluidic devices, captured microorganisms are bound to a surface of the device so the sample fluid can be removed by simply letting it flow away from the surface where the microorganisms are bound. For magnetic nanoparticles or micron beads, magnets may be employed to effect separation of the bound microorganisms from the sample.

Analyzing the labeled live microorganism to identify it may be accomplished by any suitable method, for example polymerase chain reaction (PCR) analysis or antibody labeling. For PCR analysis the live microorganism is preferably separated from the sample so that dead microorganisms or microorganisms that did not otherwise incorporate the reactive chemical label would not contaminate the analysis. When PCR is to be used for analysis, the reporter and/or capture element is preferably both a reporter and a capture element to facilitate separation of the live labeled microorganism from the sample.

For antibody labeling, a dual labeling method may be applied. A first label is the reactive chemical label that is incorporated into the microorganism when the biomolecular precursor labeled with the reactive chemical label is used to build biomolecules in the microorganism. The reactive chemical label reacts with the reporter element and the first label may therefore be used to identify which of the microorganisms in the sample are alive. To determine the identity of the live microorganisms in view of having determined which microorganisms are alive, a second label comprising a strain-specific antibody may be used to label a specific strain. The presence of the strain-specific antibody on the live microorganism may be detected by any suitable method, for example detecting the presence of a second reporter element (e.g. a bead or another antibody) used with the second label. Detection of the second reporter element on the microorganism thereby identifies the microorganism as the strain to which the antibody is specific. A plurality of different strain-specific antibody labels may be employed for identifying different microorganisms. The antibody labeling method of identification does not necessarily require separation of the live microorganism from the sample, therefore the reporter and/or capture element for the bio-orthogonal reaction with the reactive chemical label need only be a reporter element.

In a variation of the antibody labeling method for identifying the live microorganisms, a surface (e.g. a bead, microfluidic device, etc.) with immobilized strain-specific antibody may be used to capture the strain specifically. In this case, the reporter and/or capture element for the bio-orthogonal reaction with the reactive chemical label also only needs to be a reporter element since capture of live microorganism is accomplished by the strain-specific antibody immobilized on the surface. Thus, the reporter element bound to the reactive chemical label serves to identify which microorganisms are alive while the presence of the so identified live microorganism bound to the surface serves to identify the microorganism as belonging to the strain for which the antibody is specific. As previously indicated, the reporter and/or capture element itself may comprise a strain-specific antibody for the purpose of identifying the specific strain, in which case only a single label is required and the reporter and/or capture element is both a reporter and capture element.

Microorganisms of interest may include bacteria, yeast and protozoa. The present invention is especially suited to diverse species of bacteria that pose a public health risk including *E. coli* and *Listeria* spp. Suitable growth conditions are generally known in the art for specific microorganisms of interest.

Any type of sample, for example soil, food and water samples, may be analyzed for live microorganisms using the present invention. Of particular note are food and water samples. Some preliminary processing of samples may be required depending on the specific analytical technique being used to analyze for and determine the identity of the microorganism of interest. Such processing steps are well known to one skilled in the art.

The present invention also encompasses kits comprising a biomolecular precursor labelled with a reactive chemical label, a reporter/capture element bearing a functional group that reacts with the reactive chemical label, a vessel for growing the microorganism of interest and conducting a reaction between the labeled biomolecular precursor and the functionalized reporter/capture element, growth medium for a microorganism of interest, nutritional factors necessary for growing the microorganism of interest, and instructions for using the kit to identify the microorganism of interest. The kit may further include means for collecting samples and means for analyzing the microorganism of interest.

The invention can specifically identify live microorganisms from dead ones in a sample, thereby reducing the possibility of false identification of contaminating microorganisms. Further, the present method is not only able to identify live microorganisms for further characterization, but can also detect specific strains using tailored metabolites that are specific for a given microorganism. In addition, contamination of a sample after incorporation of the labeled biomolecular precursor does not interfere with the identification of the microorganisms of interest since the later microorganisms will not have incorporated any of the biomolecular precursor and may be physically separated from the microorganisms of interest. Furthermore, because metabolic incorporation of the labeled biomolecular precursor is rapid, identification of microorganisms can be done in a timely manner (within an 8-hour work day) and on-site if desired. This is in contrast to currently used cell culture-based methods, which require at least 72 hours to do and as long as 5-9 days. The present invention is a significant advantage to regulators who often need timely information to assess outbreaks and whether any legal action needs to be taken.

The present invention is of particular use for detection and identification of pathogenic bacteria in food and water, rapid detection of multiple pathogens in food samples and rapid identification of bacterial outbreaks in a healthcare setting. Functionalized amino acids may be incorporated into expressed surface proteins, which allow for not only detection and capture of living bacteria, but allows for downstream identification of the labeled bacterial strain. Furthermore, additional biomolecular precursors can be included to achieve a dual labelling strategy and enhance detection of specific strains of living bacteria.

BRIEF DESCRIPTION OF THE DRAWINGS

In order that the invention may be more clearly understood, present embodiments thereof will now be described in detail by way of example, with reference to the accompanying drawings, in which:

FIG. 1A: General metabolic labeling scheme for fluorescence labeling of live bacteria.

FIG. 1B: General dual metabolic labeling scheme for fluorescence labeling and capture of live bacteria via the metabolic label. This can be performed in any order, and is not limited to the capture method used as an example.

DESCRIPTION OF PREFERRED EMBODIMENTS

1. Metabolic Labeling

A general scheme for metabolic labeling is shown in FIG. 1A, in which living bacteria are cultured in the presence of a biomolecular precursor containing a reactive functional group, thus referred to as a "metabolic label", then reacted with a reporter element containing a paired functional group (a fluorophore, for example) to identify living cells that have incorporated the metabolic label. The following examples illustrate embodiments of the invention based on different metabolic labeling strategies.

2. Metabolic Labeling with Methionine Analogues

Figure 2:
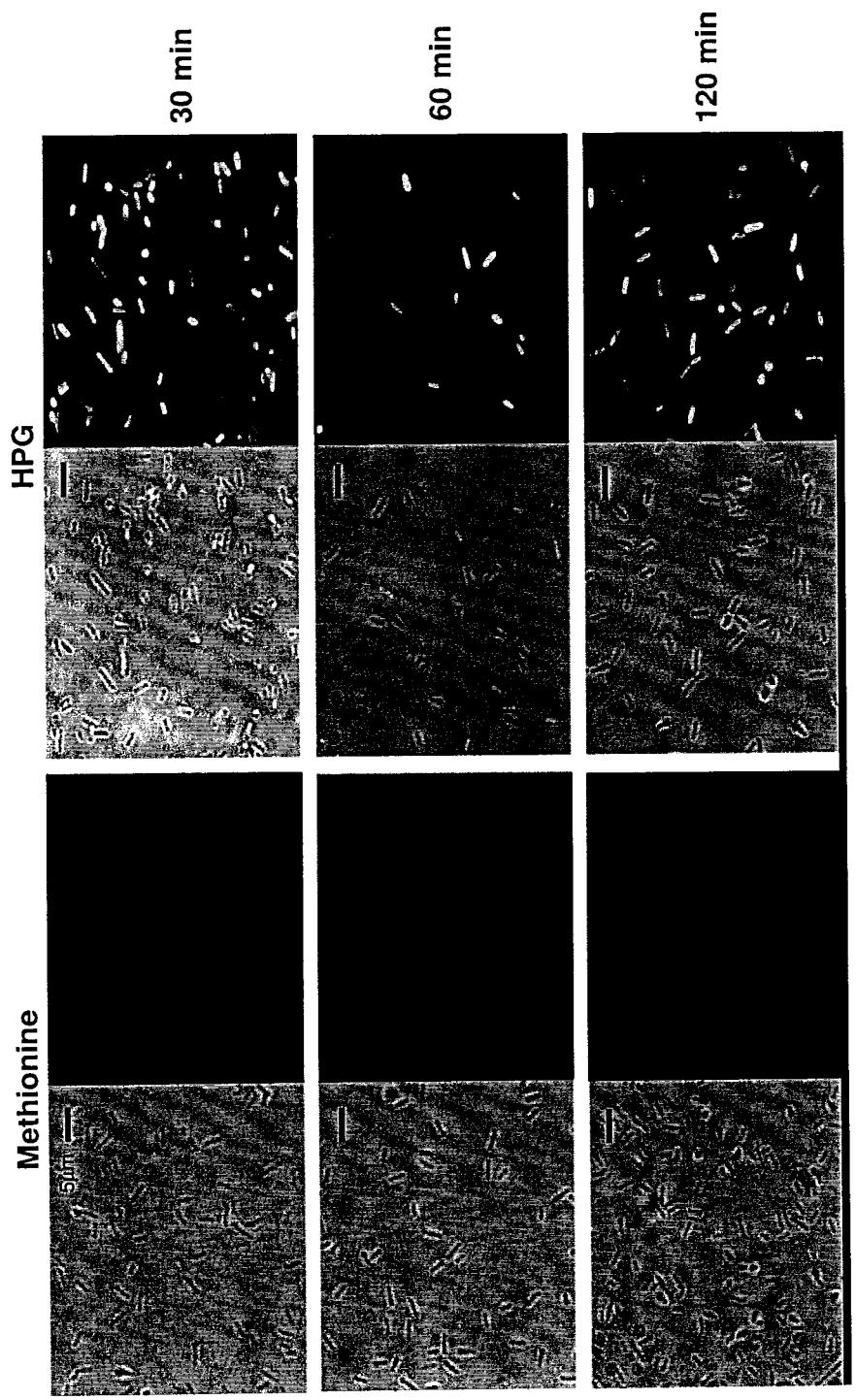
FIG. 2: Unnatural amino acid incorporation and fluorescence labeling of live lab strain *E. coli*. BL21 *E. coli* were cultured in the presence of methionine or its analogue, homopropargylglycine (HPG), as well as methionine biosynthesis inhibitory amino acids (lysine, threonine, phenylalanine, isoleucine, leucine and valine) for the indicated time points, reacted with Alexa488-azide and detected by fluorescence microscopy. Bright field is shown on the left, fluorescence is shown on the right for each condition.

Identification of Living Cells by Targeting Expressed Protein with Methionine Analogues Metabolic labeling of expressed protein with an alkyne or azide functionalized methionine analogue has previously been demonstrated in genetically modified methionine auxotrophic *E. coli* cells (Link 2003; Beatty 2005), but not for un-modified wild-type bacterial strains capable of synthesizing methionine on their own. Living pathogen detection by metabolic labeling of proteins, therefore, requires a strategy to force acquisition of the amino acid analogue from the growth medium. Using a method similar to selenomethionine labeling described for X-ray crystallography protein structure determination (Van Duyne 1993), *E. coli* cells were induced to acquire methionine and its alkyne analogue, HPG, from the medium through feedback inhibition of methionine biosynthesis. Briefly, BL21 *E. coli* cells, which are not methionine auxotrophs, were inoculated into M9 media and cultured until an OD of about 0.5 was reached, and methionine biosynthesis was inhibited by the addition of the following amino acids: lysine (100 µg/ml), threonine (100 µg/ml), phenylalanine (100 µg/ml), isoleucine (50 µg/ml), leucine (50 µg/ml) and valine (50 µg/ml). Cultures were either supplemented with methionine (50 µg/ml) or HPG (50 µg/ml) and cultured for 30 min to 16 h at 37° C. The cells were then washed in PBS and reacted with 50 µM Alexa488-azide using copper-histidine catalyzed click chemistry. Briefly, a solution containing 100 µM $CuSO_4$, 200 µM L-histidine, 2 mM sodium ascorbate, and 25 µM Alexa488-azide in PBS was incubated with the cells for 30 minutes at 37° C. Cells were washed in PBS to remove unreacted reagents, then imaged using fluorescence microscopy. Fluorescence was normalized to cells treated with the same conditions, but grown in the presence of methionine. FIG. 2 shows that not only do *E. coli* cells acquire HPG from the media and incorporate the methionine analogue in expressed protein, this can occur in as little as 30 minutes.

Figure 3:
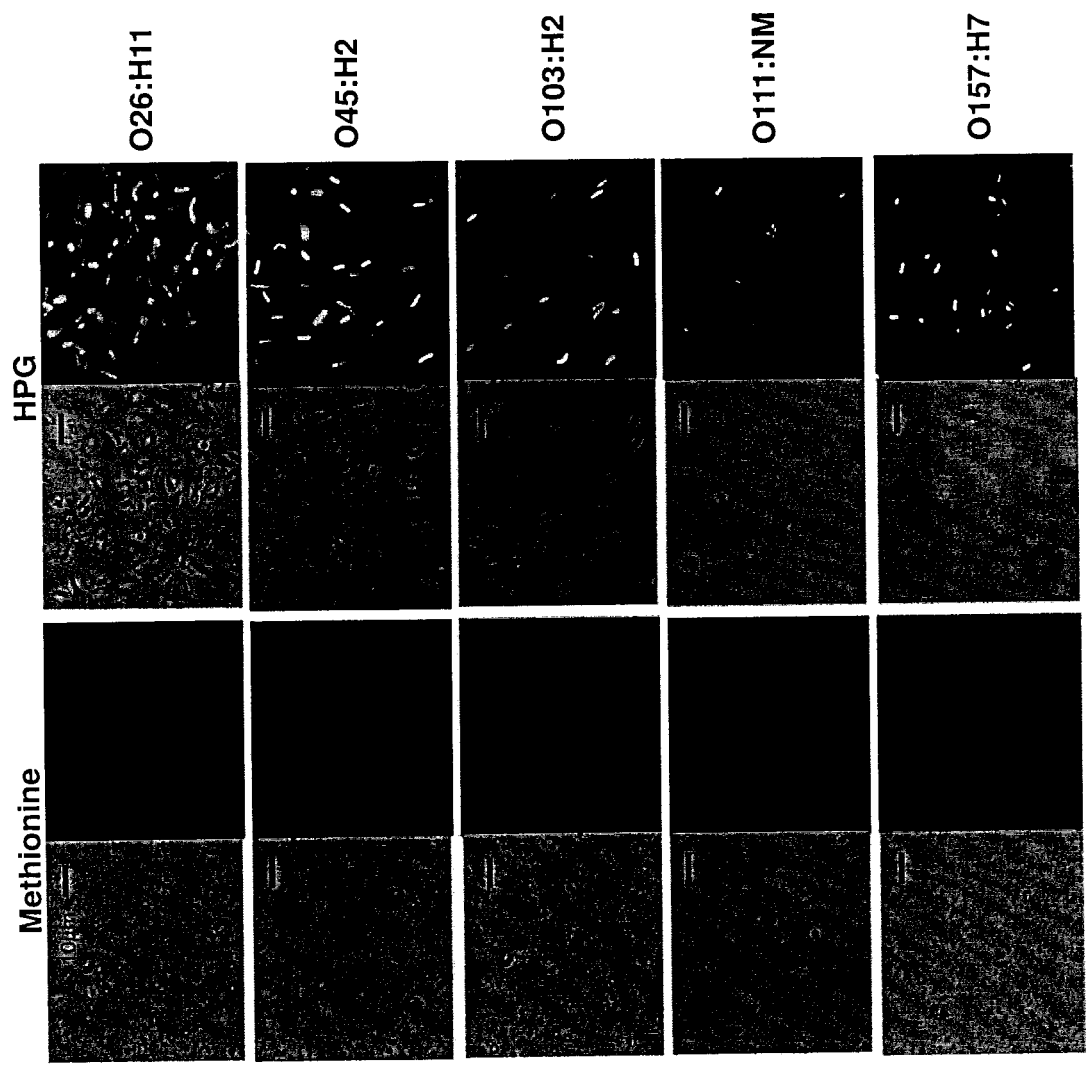
FIG. 3: Unnatural amino acid incorporation and fluorescence labeling of live verotoxigenic *E. coli* (VTEC). VTEC strains with serotypes O26:H11, O45:H2, O103:H2, O111:NM and O157:H7 were cultured in the presence of methionine or HPG, as well as methionine biosynthesis inhibitory amino acids (lysine, threonine, phenylalanine, isoleucine, leucine and valine) overnight, reacted with Alexa488-azide and detected by fluorescence microscopy. Bright field is shown on the left, fluorescence is shown on the right for each condition.
Figure 4:
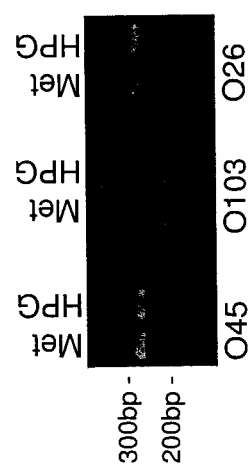
FIG. 4: Metabolic labeling and click chemistry of living VTEC does not interfere with downstream strain identification by PCR. Strain-specific PCR products were amplified from VTEC strains (O45:H2, 255 bp; O103:H2, 205 bp; O26:H11, 283 bp) and detected by agarose gel, after being cultured in the presence of methionine or HPG then reacted with Alexa488-azide by copper catalyzed click chemistry.

Similar to lab strain BL21 *E. coli*, pathogenic, verotoxin producing *E. coli* (VTEC) cells were metabolically labeled by the unnatural methionine analogue. VTEC strains inoculated directly and cultured overnight in M9 media containing HPG and methionine biosynthesis inhibition amino acids were fluorescently labeled after being reacted with Alexa488-azide (FIG. 3), as described above. Similar to BL21 *E. coli*, metabolic label incorporation was also detected after 30 minutes of contact between HPG and the VTEC strain O45:H2. Furthermore, downstream identification by strain-specific PCR was not affected by treating the cells using this method (FIG. 4). This demonstrates the robust nature of unnatural amino acid metabolic labeling as it can apply to both lab strain and pathogenic strains of *E. coli*, and will serve as a valuable tool for identification of living contaminating bacteria.

Figure 5:
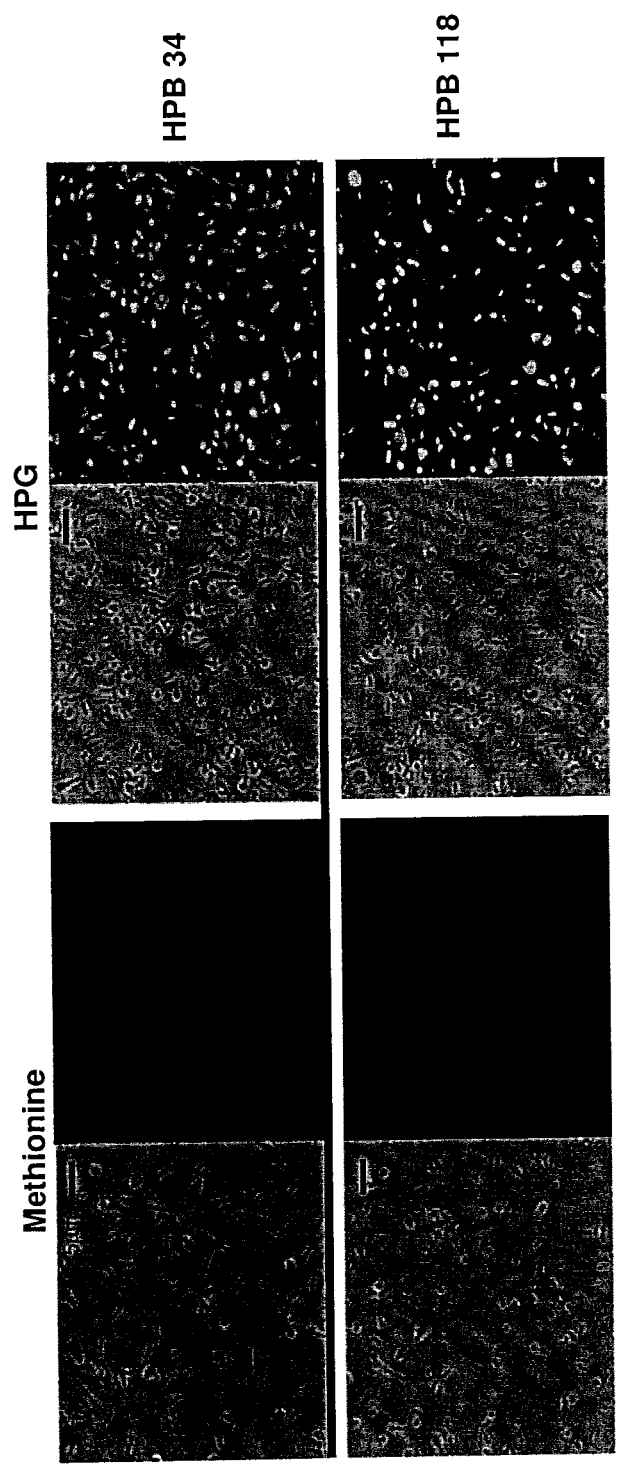
FIG. 5: Unnatural amino acid incorporation and fluorescence labeling of live *Listeria innocua* strains. *L. innocua* strains HPB 34 and 118 were cultured in the presence of methionine or HPG, as well as methionine biosynthesis inhibitory amino acids (lysine, threonine, phenylalanine, isoleucine, leucine and valine) overnight, reacted with Alexa488-azide and detected by fluorescence microscopy. Bright field is shown on the left, fluorescence is shown on the right for each condition.

In addition to gram negative *E. coli* strains, gram positive *Listeria* strains were investigated to probe the diversity of bacteria susceptible to this labeling strategy. Two strains of *Listeria innocua* were cultured in HTM minimal medium containing the methionine biosynthesis inhibition amino acids, in the presence of methionine (100 µg/ml) or HPG (100 µg/ml) for 16 h at 30° C., then reacted with Alexa488-azide as described earlier. As shown in FIG. 5, the tested gram positive strains were labeled efficiently, highlighting this as a robust labeling strategy that applies to both gram negative and gram positive species.

Figure 6:
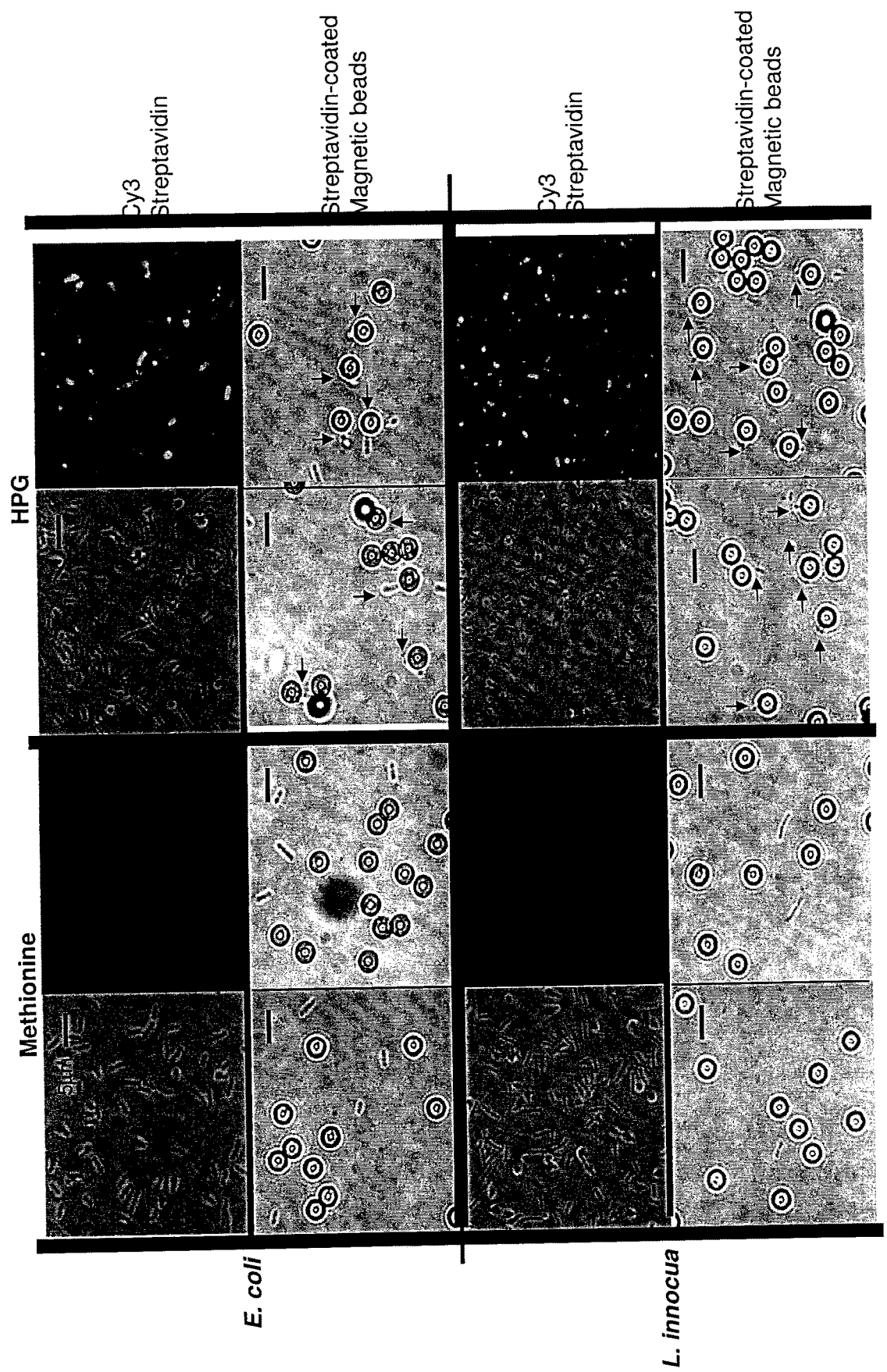
FIG. 6: Capture via unnatural amino acid metabolic labeling of live gram negative (*E. coli*) and gram positive (*L. innocua*) bacteria. BL21 *E. coli* or *L. innocua* were cultured in the presence of methionine or HPG, as well as methionine biosynthesis inhibitory amino acids (lysine, threonine, phenylalanine, isoleucine, leucine and valine) overnight, reacted with biotin-azide and either detected by fluorescence microscopy after incubation with Cy3-streptavidin (top panels), or captured after incubation with streptavidin-coated magnetic beads (bottom panels, red arrows).

E. coli and L. innocua cells metabolically labeled by HPG were further investigated to determine if they could be captured on a surface via the incorporated amino acid analogue. To test this, bacteria cultured in the presence of methionine or HPG were reacted with biotin-azide (100 µM) using copper-histidine catalyzed click chemistry, as described, then washed in PBS and incubated with either streptavidin-Cy3 or streptavidin-coated magnetic beads (M280 Dynabeads, Invitrogen) for 1 hour at room temperature. Fluorescent labeling was achieved through the biotin/streptavidin interaction (FIG. 6), which reveals that sites of HPG incorporation (and thus biotinylation) are accessible for the bulky streptavidin to bind. This labeling is reflected in the capture panels, which show multiple E. coli and L. innocua cells bound to the streptavidin coated beads when bacteria are cultured in the presence of HPG. To our knowledge, this is the first example demonstrating bacterial capture using a metabolic label.

3. Metabolic Labeling with KDO Analogues

Synthesis of Labeled KDOs

Scheme 1 provides a synthetic scheme for preparing various functionalized 3-deoxy-D-manno-oct-2-ulosonic acid analogues.

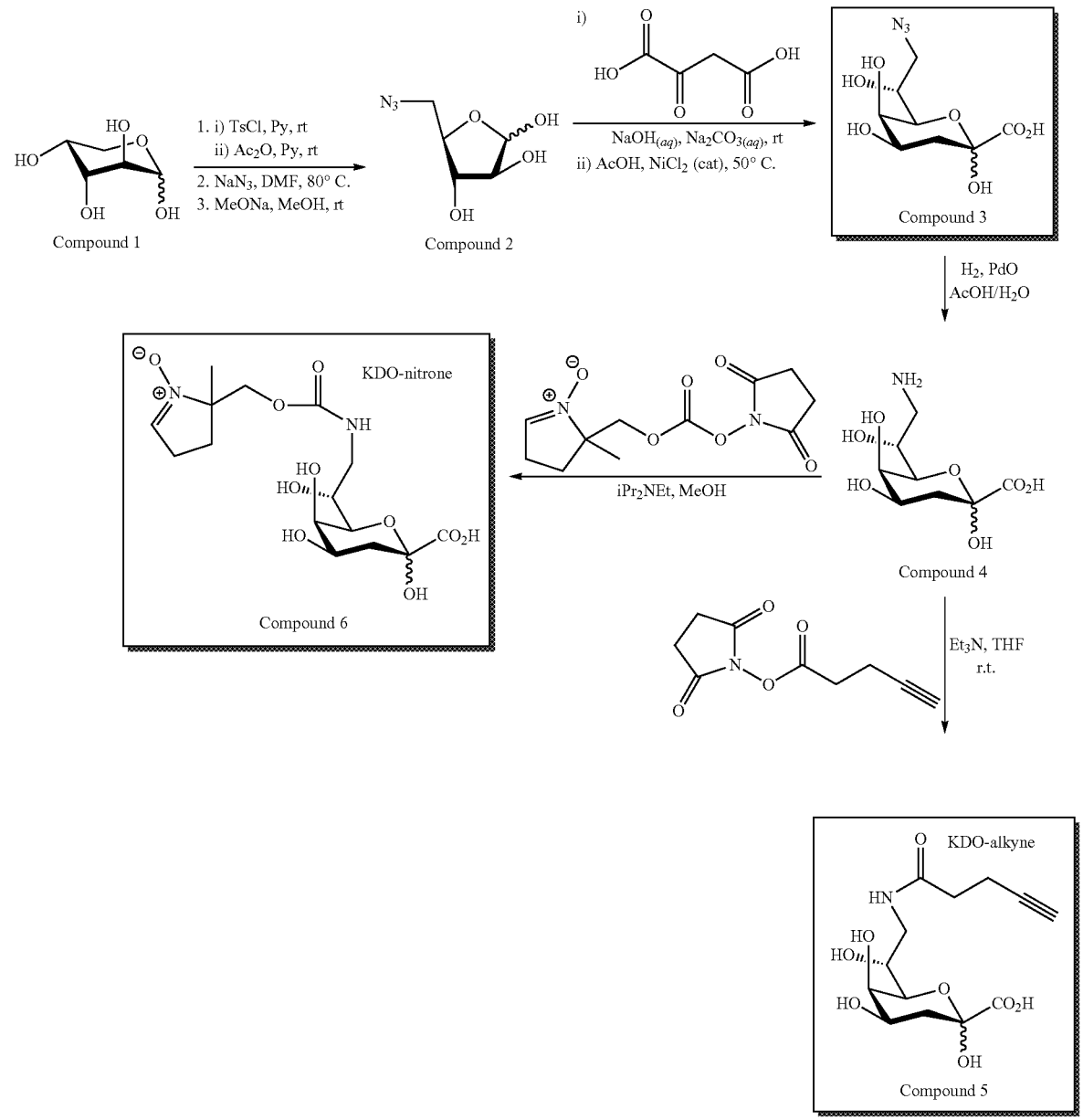

Scheme 1 - Synthesis of KDO-azide, KDO-alkyne and KDO-nitrone

Compound 1 to Compound 2

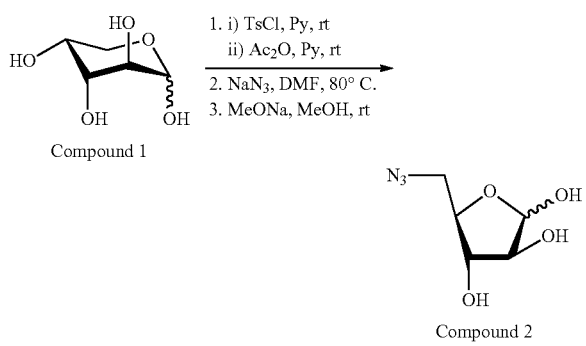

A mixture of D-(−)-Arabinose (5.17 g, 34.4 mmol, 1.0 eq) and pyridine (35.0 mL, 0.43 mol, 12.0 eq) was heated at 100 °C for 2 hours, cooled to room temperature and treated with TsCl (7.22 g, 37.8 mmol, 1.1 eq). The reaction was stirred at room temperature for 16 hours, acetic anhydride (17.0 mL, 0.18 mol, 5.2 eq) was added and the reaction was monitored by TLC. Upon complete acylation, the mixture was concentrated at reduced pressure and azeotroped with toluene. The residue was dissolved in DMF, NaN$_3$ (4.48 g, 68.8 mmol, 2.0 eq) was added and the suspension was stirred at 80 °C for 20 hours. The reaction was cooled to room temperature, diluted with ethyl acetate (400 mL) and washed with water. Organic layer was dried over magnesium sulfate and concentrated under reduced pressure. The crude was purified by column chromatography (Hex:EtOAc/7:3, $R_f$=0.7) to yield acetylated Compound 2 as yellow oil (71.0 mg, 12%). To the solution of acetylated Compound 2 (1.24 g, 4.12 mmol, 1.0 eq) in methanol (2 mL) was added NaOMe (22.0 mg, 0.41 mmol, 0.1 eq) at room temperature and the reaction was stirred under argon for 3 hours. The reaction was neutralized with Dowex 50 (H$^+$) and filtered. The filtrate was concentrated, re-suspended in ethyl acetate (125 mL) and filtered again. Solvent was removed under reduced pressure to yield pure Compound 2 as yellow oil (658.0 mg, 91%).

Compound 2 to Compound 3

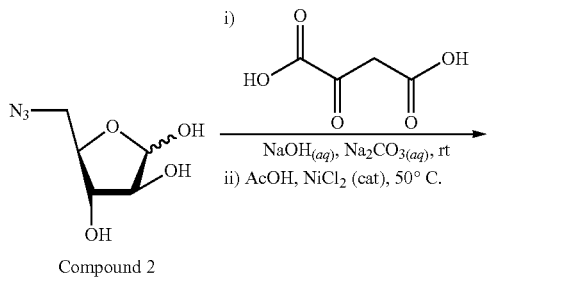

To a solution of Compound 2 (324.0 mg, 1.85 mmol, 1.0 eq) in water (4.3 mL) was added sodium carbonate (491 mg, 4.67 mmol, 2.8 eq). Oxaloacetic acid (293.0 mg, 2.22 mmol, 1.2 eq) was added portion-wise at room temperature over 5 minutes and the pH was adjusted to pH 11 using 10 M aqueous sodium hydroxide solution. The reaction was stirred at room temperature for 2 hours and then acidified to pH 5 using acetic acid. NiCl$_2$ (2.5 mg, 0.0185 mmol, 0.01 eq) was added and the mixture was heated to 50 °C for 1 hour. The mixture was cooled to room temperature, concentrated under reduced pressure and purified by column chromatography 0-20% water in isopropanol (H$_2$O:/PrOH/1:4, $R_f$=0.5) to yield Compound 3 as tan solid (433.0 mg, 89%). MS (ESI−) calcd (C$_8$H$_{13}$N$_3$O$_7$): 262.07 [M−H]$^-$, found 262.2.

Compound 3 to Compound 4

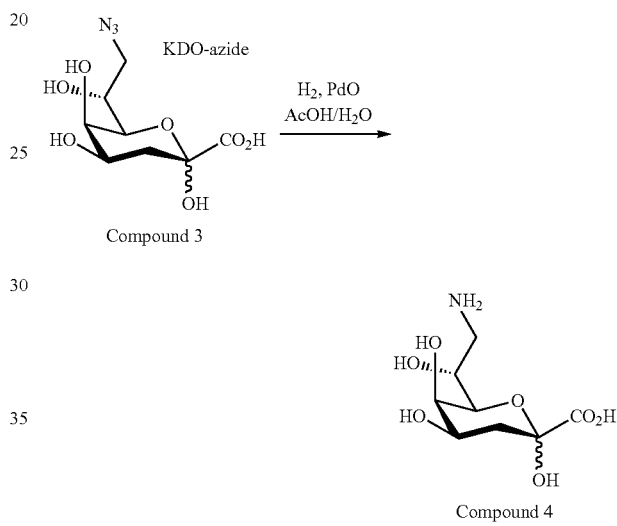

To a solution of Compound 3 (433.0 mg, 1.65 mmol, 1.0 eq) in water (16.7 mL) and acetic acid (20 drops) was added palladium oxide (109.0 mg, 0.89 mmol, 0.54 eq). Hydrogen gas was bubbled through the reaction and the solution was stirred under hydrogen gas over 23 hours. Solid was filtered off over Celite under vacuum, the cake rinsed once with water. Filtrate was concentrated and further dried on the high vacuum pump to yield crude Compound 4 as yellow solid. (H$_2$O:/PrOH/1:9, $R_f$=0.25). Crude Compound 4 was immediately used in the next reaction without further purification. MS (ESI+) calcd (C$_8$H$_{15}$NO$_7$): 237.08 [M+H]$^+$, found 238.2.

Compound 4 to Compound 5

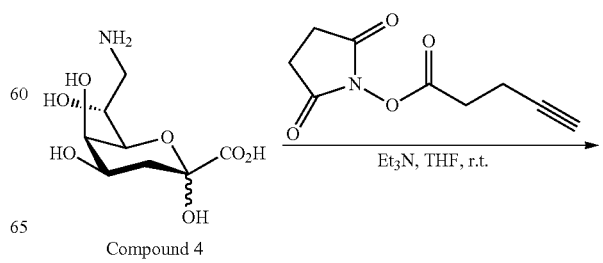

-continued

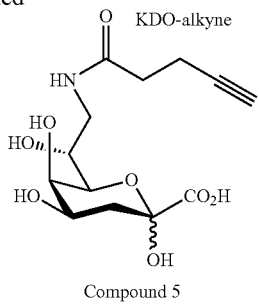

Compound 5

Compound 4 (crude, 1.6 mmol) was dissolved in THF (8.24 mL), NHS-alkyne (320.0 mg, 1.65 mmol, 1.0 eq) and triethylamine (2.76 mL, 19.8 mmol, 12.0 eq) were added and the solution was stirred at room temperature under argon for 43 hours. The solution was concentrated under reduced pressure to a yellow solid, which was stored under argon at −78° C. The crude was purified by preparatory HPLC using gradient of 5-25% MeCN/H$_2$O (F.A 0.01%) over 10 minutes. Eluted fractions were confirmed by the MS, combined and concentrated under reduced pressure to yield Compound 5 as red foam (71.0 mg, 13.7%). MS (ESI−) calcd ($C_{13}H_{19}NO_8$): 316.10 [M−H]$^-$, found 316.1.

Compound 4 to Compound 6

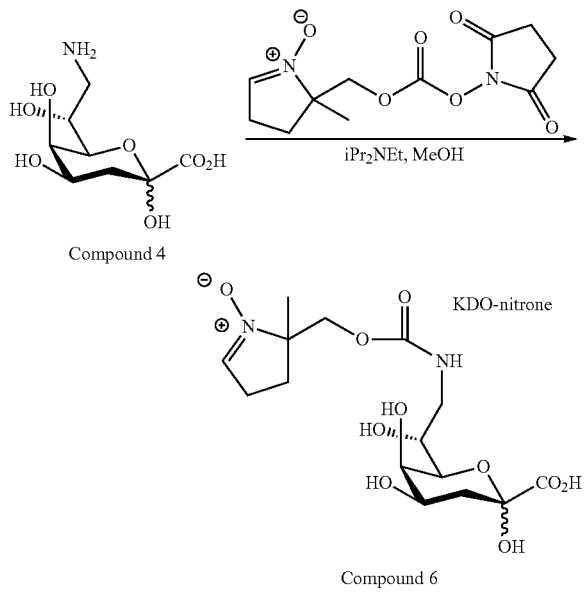

Compound 6

To a suspension of KDO—NH2 in methanol was added iPr$_2$NEt until basic pH was achieved. Nitrone-succinimide was added drop wise over 5 minutes at room temperature. Reaction was stirred at r.t. for 4 hours. The yellow suspension was concentrated and stored under argon at −78° C. The mixture was purified by preparatory HPLC using 2% MeCN/98% H$_2$O (F.A 0.01%) for 3.5 minutes, then 5% MeCN/95% H$_2$O (F.A 0.01%). Eluted fractions were confirmed by the MS. Product obtained as off-white solid (62.0 mg, 16.5%). HRMS m/z calcd ($C_{15}H_{24}N_2O_{10}$) [M+Na]$^+$,: 415.13293, found 415.13232.

Identification of Living Cells by Targeting LPS with KDO Analogues

KDO-azide has been shown to be incorporated into the LPS molecules in the outer membrane of gram negative bacteria (Dumont 2012). To determine if bacteria could be labeled using bio-orthogonal reaction conditions with minimal cell toxicity (Kennedy 2011), as above, BL21 E. coli were inoculated into minimal medium containing 4 mM KDO analogue and cultured for 16 h at 37° C. The cells were then washed in PBS and reacted with 25 μM Alexa488-alkyne (for KDO-azide or KDO-nitrone, FIG. 7A), 25 μM Alexa488-azide (for KDO-alkyne, FIG. 7A) or 50 μM coumarin-azide (for KDO-alkyne, FIG. 8) using copper-histidine catalyzed click chemistry. Briefly, a solution containing 100 μM CuSO$_4$, 200 μM L-histidine, 2 mM sodium ascorbate, and 25 μM Alexa488-azide (or Alexa488-alkyne) in PBS was incubated with the cells for 30 minutes at 37° C. Cells were washed in PBS to remove unreacted reagents, then imaged using fluorescence microscopy. Fluorescence was normalized to cells treated with the same conditions, but grown in the absence of functionalized KDO.

Figure 7A:
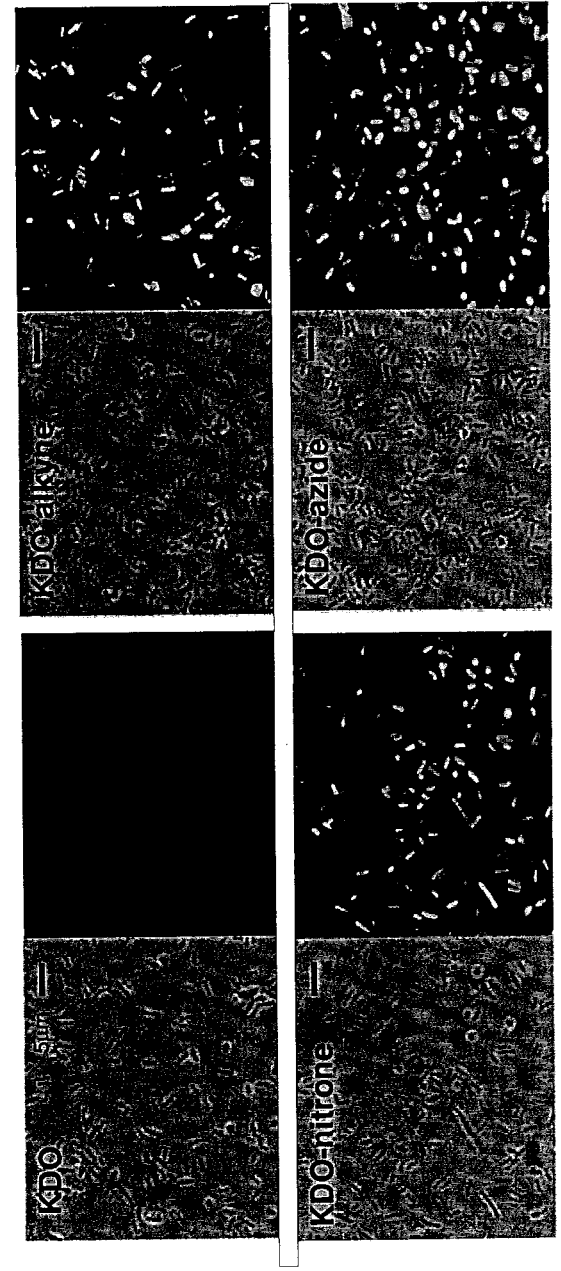
FIG. 7A: Unnatural sugar incorporation and fluorescence labeling of live lab strain *E. coli*. BL21 *E. coli* were cultured in the presence of 3-deoxy-D-manno-oct-2-ulosonic acid (KDO) or functionalized KDO sugar overnight, reacted with Alexa488-alkyne or Alexa488-azide and detected by fluorescence microscopy. Bright field is shown on the left, fluorescence is shown on the right for each condition.
Figure 8:
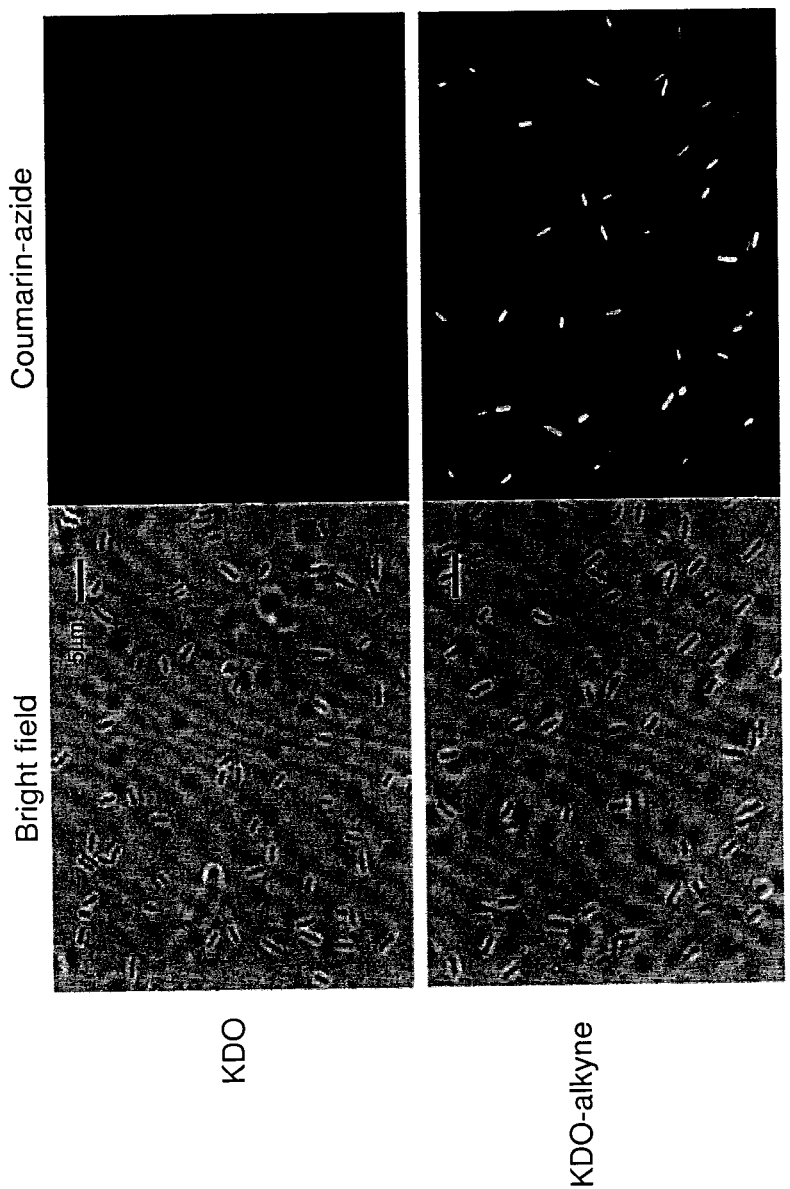
FIG. 8: Unnatural sugar incorporation and fluorogenic detection of BL21 *E. coli* after culture in the presence of KDO or KDO-alkyne overnight, and reaction with coumarin-azide.

KDO-alkyne and KDO-nitrone were synthesized for this invention and shown to be incorporated into E. coli LPS molecules (FIG. 7A). KDO-alkyne is of great interest as it can be reacted with fluorogenic coumarin-azide (FIG. 8), which does not fluoresce until cycloaddition has occurred. This reduces the need for multiple washes that are required to limit background fluorescence when a fluorophore (like Alexa488) is used in the click reaction.

Figure 7C:
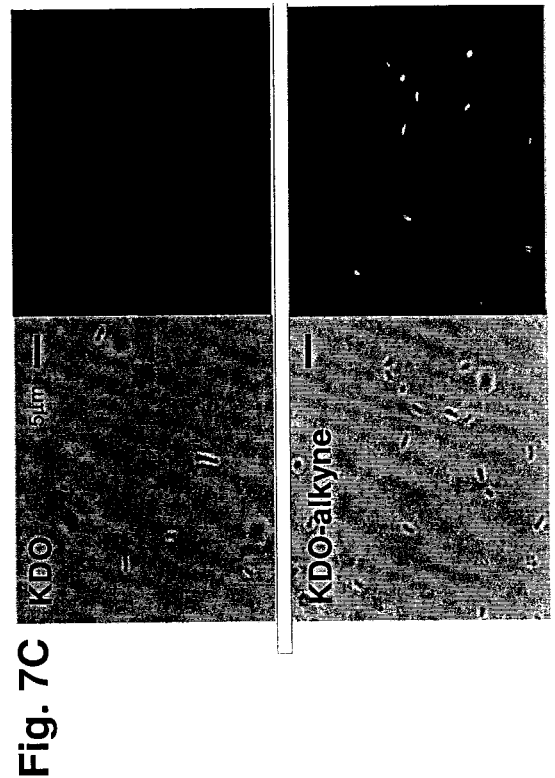
FIG. 7C: Unnatural sugar incorporation and fluorescence labeling of BL21 *E. coli* after culture for five hours in phosphate-buffered saline in the presence of KDO or KDO-alkyne and reaction with Alexa488-azide.
Figure 7B:
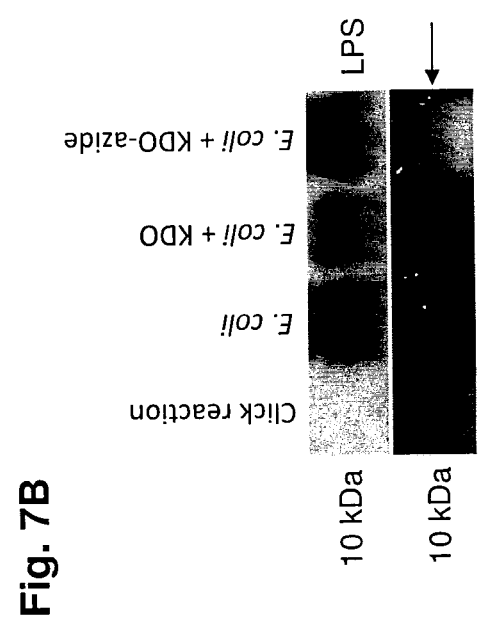
FIG. 7B: LPS gel confirming KDO-azide incorporation into LPS molecules of BL21 *E. coli*. LPS were extracted after culture in the presence or absence of KDO or KDO-azide overnight, and fluorescence labeling by Alexa-alkyne was detected by SDS-PAGE. LPS silver stain is shown above and in-gel fluorescence is shown below.

Metabolic incorporation of the metabolic label and fluorescent labeling of BL21 E. coli cells was achieved in under seven hours for the KDO analogue. E. coli cells inoculated into minimal medium or PBS containing functionalized KDO (e.g. KDO-alkyne in FIG. 7C) were cultured for 5 h at 37° C., washed in PBS, then fluorescently labeled using copper-histidine catalyzed click chemistry as described. Fluorescent signal was detected above background for bacteria cultured in the presence of functionalized KDO. Since E. coli cells incorporated KDO-alkyne while suspended in PBS, it may be possible to initiate contact between contaminating bacteria and the metabolic label during early steps of sample preparation, such as sorting bacteria from food particulates.

Figure 9:
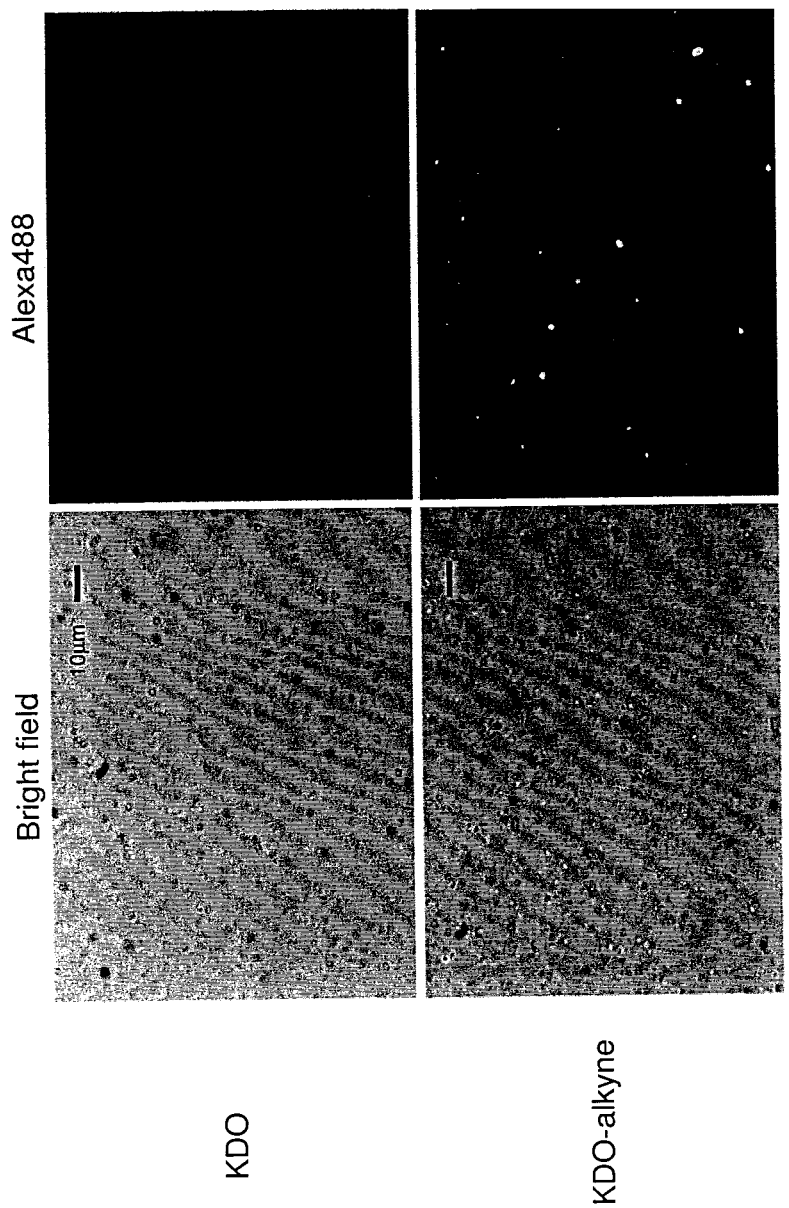
FIG. 9: Unnatural sugar incorporation and fluorescence labeling of live VTEC strain O45:H2 after culture in the presence of KDO or KDO-alkyne overnight, and reaction with Alexa488-azide.

Metabolic labeling of VTEC was also investigated to determine if this labeling strategy could be applied to the detection of live pathogenic bacteria. FIG. 9 shows the VTEC strain of serotype O45:H2 is capable of incorporating KDO-alkyne into LPS molecules, as detected by fluorescence microscopy after cells were reacted with Alexa488-azide. Therefore, targeting LPS of bacteria with a KDO analogue can also be used to identify contamination by living pathogenic strains of E. coli.

4. Dual Metabolic Labeling of Living Bacteria

Figure 10:
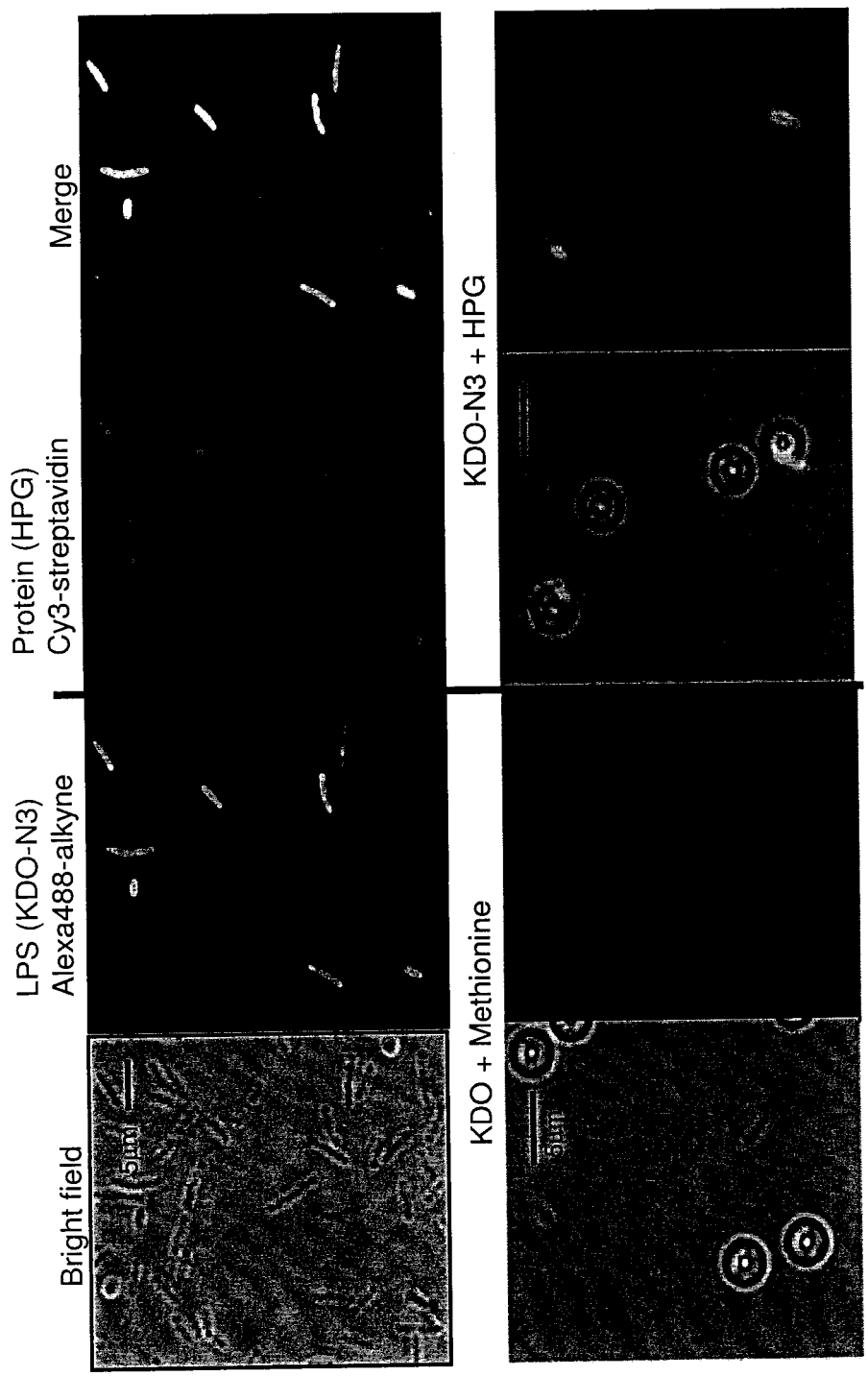
FIG. 10: Dual metabolic label incorporation, fluorescence labeling and capture of live lab strain *E. coli*. BL21 *E. coli* were cultured in the presence of methionine and KDO or HPG and KDO-azide, as well as methionine biosynthesis inhibitory amino acids (lysine, threonine, phenylalanine, isoleucine, leucine and valine) overnight. The cells were first reacted with biotin-azide to biotinylate surface proteins, then reacted with Alexa488-alkyne to fluorescently label LPS molecules. Surface biotinylation was either fluorescently detected after incubation with Cy3-streptavidin (top panels), or bacteria were captured after incubation with streptavidin-coated magnetic beads (bottom panels). Fluorescence levels are adjusted above background detected for cells grown in the presence of KDO and methionine.

Living bacteria cultured in the presence of two metabolic labels, such as HPG and KDO-azide, are capable of incorporating both for a dual metabolic labeling strategy shown in FIG. 1B. Beyond identification of living cells, this method has the potential to discriminate between gram positive and gram negative bacteria as functionalized KDO will only be incorporated into LPS of gram negative cells, whereas HPG should not discriminate between the two. This method may also be used to capture living bacteria via incorporation of HPG, and fluorescent identification of gram negative strains via incorporation of KDO-azide. To demonstrate this, BL21 E. coli were inoculated into M9 media containing KDO-azide or KDO, then cultured for 6-7 hours. Methionine biosynthesis was then inhibited and either methionine or HPG were added to the cultures and incubated for 16 hours. Cells were reacted with biotin-azide to label surface proteins containing HPG, then reacted with Alexa488-alkyne to fluorescently label LPS containing KDO-azide. The bacteria were then incubated with either Cy3-streptavidin to fluorescently label surface proteins, or with streptavidin-coated magnetic beads to capture the dual metabolically labeled cells via the incorporated HPG label (FIG. 10). Using the dual metabolic labeling strategy, there is additional confirmation that the bacteria are living, if labeling gram negative strains, while providing a screen for gram positive vs. gram negative strains as gram positive will only incorporate the unnatural amino acid analogue.

5. Immunocapture and Metabolic Labeling of Living Bacteria

Figure 11:
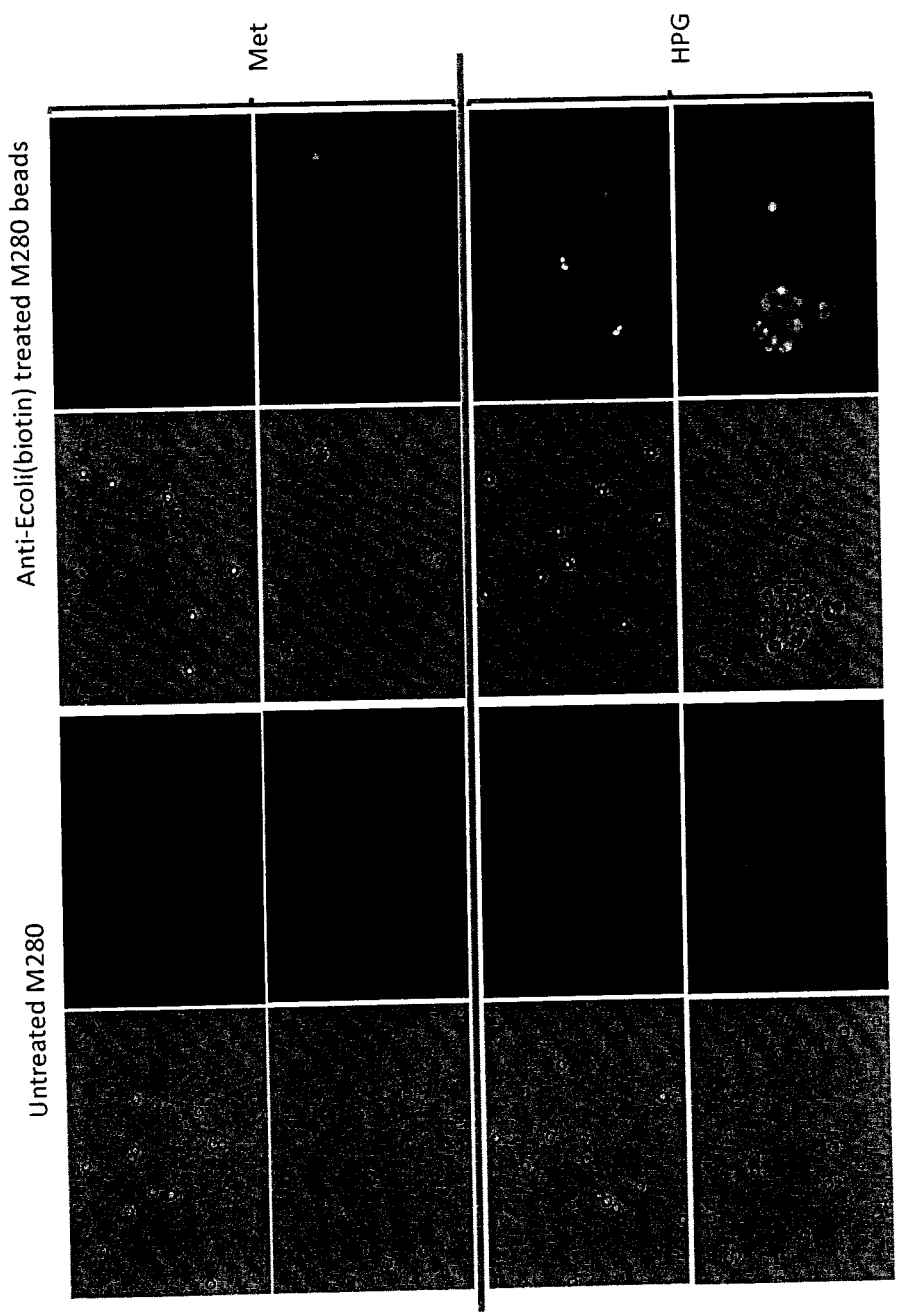
FIG. 11: Metabolic label incorporation, immunocapture and fluorescence identification of live K12 strain *E. coli*. K12 *E. coli* were cultured for 30 minutes in M9 minimal media, in the presence of methionine ("Met") or HPG, as well as methionine biosynthesis inhibitory amino acids (lysine, threonine, phenylalanine, isoleucine, leucine and valine). M280 streptavidin-coated magnetic beads treated with PBS ("Untreated") or PBS containing biotin-tagged Anti-*E. coli* antibody were then added to the culture for 1 hour before the beads were washed in PBS and reacted with Alexa488-azide to fluorescently label surface proteins. Fluorescence levels are adjusted above background detected for cells grown in the presence of methionine.

Metabolic labeling is compatible with strain-specific immunocapture using magnetic beads coated with antibodies directed to specific bacteria. This method has the potential to concentrate specific strains of bacteria from food or water samples, while simultaneously allowing bacteria to acquire the functionalized biomolecular precursor and incorporate it in target biomolecules. Captured bacteria are then identified as living or dead by a subsequent bioorthogonal reaction and detection by fluorescence microscopy. To demonstrate this, K12 *E. coli* were cultured in M9 media with methionine or HPG after methionine biosynthesis was inhibited. M280 magnetic beads treated with PBS or biotin-tagged anti-*E. coli* antibody were co-incubated with the *E. coli*. Bacteria/bead aggregates were washed in PBS, then reacted with Alexa488-azide to fluorescently identify living bacteria captured on the M280 magnetic beads. Only beads treated with anti-*E. coli* antibody captured bacteria, that were identified as being alive in the samples treated with the HPG metabolic label, as shown in FIG. 11.

REFERENCES

The contents of the entirety of each of which are incorporated by this reference.

Akihiko M. (1995) Culture Medium for Identifying Bacterium and Method for Identifying Bacterium. Japanese Patent Publication JP 07-023794 published Jan. 27, 1995.

Allen J J, Lazerwith S E, Shokat K M. (2005) Bio-orthogonal Affinity Purification of Direct Kinase Substrates. *J Am Chem Soc.* 127(15), 5288-5289.

Beatty K E, Xie F, Wang Q, Tirrell D A. (2005) Selective Dye-Labeling of Newly Synthesized Proteins in Bacterial Cells. *J. Am. Chem. Soc.* 127, 14150-14151.

Beatty K E, Fisk J D, Smart B P, Lu Y Y, Szychowski J, Hangauer M J, Baskin J M, Bertozzi C R, Tirrell D A. (2010) Live-Cell Imaging of Cellular Proteins by a Strain-Promoted Azide-Alkyne Cycloaddition. *Chembiochem.* 11, 2092-2095.

Besanceney-Webler C, Jiang H, Wang W, Baughn A D, Peng W. (2011) *Bioorganic & Medicinal Chemistry Letters.* doi:10.1016/j.bmcl.2011.05.038.

Dieterich D C, Lee J J, Link A J, Graumann J, Tirrell D A, Schuman E M. (2007) Labeling, detection and identification of newly synthesized proteomes with bioorthogonal non-canonical amino-acid tagging. *Nature Protocols.* 2(3), 532-540.

Dukan S, Dumont A, Awwad M, Malleron A, Vauzeilles B. (2013) A method for specifically detecting living bacteria. European Patent Publication EP 2617833 published Jul. 24, 2013.

Dumont A, Malleron A, Awwad M, Dukan S, Vauzeilles B. (2012) Click-mediated labeling of bacterial membranes through metabolic modification of the lipopolysaccharide inner core. *Angew Chem Int Ed Engl.* 51(13), 3143-3146.

Fetzer I, Jehmlich N, Vogt C, Richnow H-H, Seifert D, Harms H, Bergen M von, Schmidt F. (2010) Calculation of partial isotope incorporation into peptides measured by mass spectrometry. *BMC Research Notes.* 3, 178 (9 pages).

Hang H C, Charron G, Wilson J P, Raghavan A, Zhang M, Yang Y-Y, Rangan K, Tsou L K, Yount J. (2010) Chemical Reporters of Protein Acylation. United States Patent Publication 2010/0203647 published Aug. 12, 2010.

Hannoush R N. (2010) Methods for the Detection of Fatty-Acylated Protein. United States Patent Publication 2010/0189660 published Jul. 29, 2010.

Hong H-b. (2004) Method of Detecting Microorganisms Using Labeled Electron Acceptors. United States Patent Publication 2004/0241848 published Dec. 2, 2004.

Hsu T L, Hanson S R, Kishikawa K, Wang S K, Sawa M, Wong C H. (2007) Alkynyl sugar analogs for the labeling and visualization of glycoconjugates in cells. *Proc. Natl. Acad. Sci. U.S.A.* 104, 2614-2619.

Kennedy D C, McKay C S, Legault M C, Danielson D C, Blake J A, Pegoraro A F, Stolow A, Mester Z, Pezacki J P. (2011) Cellular consequences of copper complexes used to catalyze bioorthogonal click reactions. *J. Am. Chem. Soc.* 133, 17993-18001.

Kulla H. (1994) Device and Method for the Detection of Microorganisms which Produce Low-Molecular-Weight Metabolites. U.S. Pat. No. 5,348,884 issued Sep. 20, 1994.

Kumar K, D'Alarcao M, Dafik L. (2009) Fluorinated Carbohydrates and Their Use in Tumor Visualization, Tissue Engineering, and Cancer Chemotherapy. United States Patent Publication 2009/0214439 published Aug. 27, 2009.

Lim R K V, Lin Q. (2010) Bioorthogonal Chemistry: Recent Progress and Future Directions. *Chem Commun (Camb).* 46(10), 1589-1600.

Link A J, Tirrell D A. (2003) Cell Surface Labeling of *Escherichia coli* via Copper(I)-Catalyzed [3+2] Cycloaddition. *J. Am. Chem. Soc.* 125, 11164-11165.

Link A J, Vink M K, Tirrell D A. (2004) Presentation and Detection of Azide Functionality in Bacterial Cell Surface Proteins. *J. Am. Chem. Soc.* 126, 10598-10602.

Meller A, Frank-Kamenetskii M, Wanunu M, Kuhn H, Singer A, Morrison W. (2011) Label-free Sensing of PNA-DNA Complexes Using Nanopores. International Patent Publication WO 2011/028494 published Mar. 10, 2011.

Nason F, Meighan J P. (2011) Bioluminescent Bacterial Detection. International Patent Publication WO 2011/021008 published Feb. 24, 2011.

Ngo J T, Champion J A, Mandavi A, Tanrikulu I C, Beatty K E, Connor R E, Yoo T H, Dieterich D C, Schuman E M, Tirrell D A. (2009) Cell-selective metabolic labeling of proteins. *Nat. Chem. Biol.* 5, 715-717.

Ngo J T, Tirrell D A. (2011) Noncanonical amino acids in the interrogation of cellular protein synthesis. *Acc Chem Res.* 44, 677-685.

Pollard P C. (1995) In-situ Measurement of Bacterial Growth in Wastewater Treatment Processes. International Patent Publication WO 1995/012687 published May 11, 1995.

Robillard M S, Gruell H. (2008) Targeted Imaging and/or Therapy Using the [3+2] Azide-Alkyne Cycloaddition. United States Patent Publication 2008/0267878 published Oct. 30, 2008.

Robillard M S, Robillard G T, Kocer A. (2011) Azide Modified Proteins. United States Patent Publication 2011/0064667 published Mar. 17, 2011.

Sadamoto R, Matsubayashi T, Shimizu M, Ueda T, Koshida S, Koda T, Nishimura S. (2008) Bacterial Surface Engineering Utilizing Glucosamine Phosphate Derivatives as Cell Wall Precursor Surrogates. *Chemistry.* 14(33), 10192-10195.

Thacker J. (2002) Methods for the Rapid Detection of Rapidly Respiring Microorganisms. U.S. Pat. No. 6,344,332 issued Feb. 5, 2002.

Tirrell D, Dieterich D C, Link A J, Schuman E. (2010) Use of Non-canonical Amino Acids as Metabolic Markers for Rapidly-Dividing Cells. United States Patent Publication 2010/0247433 published Sep. 30, 2010.

Van Duyne G D, Standaert R F, Karplus P A, Schreiber S L, Clardy J. (1993) Atomic structures of the human immunophilin FKBP-12 complexes with FK506 and rapamycin. *J Mol Biol.* 229(1), 105-124.

Wong C-H, Hsu T-L, Hanson S R, Sawa M. (2011) Glycoproteomic Probes for Fluorescent Imaging Fucosylated Glycans In-vivo. U.S. Pat. No. 7,910,319 issued Mar. 22, 2011.

Yang Y-Y, Ascano J M, Hang H C. (2010a) Bioorthogonal Chemical Reporters for Monitoring Protein Acetylation. *J Am Chem Soc.* 132(11), 3640-3641.

Yang Y-Y, Grammel M, Raghavan A S, Charron G, Hang H C. (2010b) Comparative Analysis of Cleavable Azobenzene-Based Affinity Tags for Bioorthogonal Chemical Proteomics. *Chemistry & Biology.* 17, 1212-1222.

Yang Y-Y, Grammel M, Hang H C. (2011) Identification of lysine acetyltransferase p300 substrates using 4-pentynoylcoenzyme A and bioorthogonal proteomics. *Bioorganic & Medicinal Chemistry Letters.* doi: 10.1016/j.bmcl.2011.05.060.

Zheng Q, Saha S, Lee L A, Barnhill H, Oxsher J, Dreher T, Wang Q. (2011) Chemoselective Modification of Turnip Yellow Mosaic Virus by Cu(I) Catalyzed Azide-Alkyne 1,3-Dipolar Cycloaddition Reaction and Its Application in Cell Binding. *Bioconjug. Chem.* 22(1), 58-66.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

What is claimed is:

1. A method of selectively identifying a live microorganism in a soil, food or water sample comprising:
   a) contacting a sample suspected of containing the live microorganism with one or more biomolecular precursors labeled with a reactive chemical label, wherein each of said one or more biomolecular precursors is labeled with the same reactive chemical label;
   b) growing the live microorganism under conditions that promote selective growth of the live microorganism to permit the live microorganism to utilize the one or more biomolecular precursors labeled with the same reactive chemical label to synthesize labeled biomolecules on a cell surface of the live microorganism to produce a labeled live microorganism;
   c) contacting the labeled live microorganism with a reporter and/or capture element bearing a functional group that reacts with the same reactive chemical label; and,
   d) analyzing the labeled live microorganism to identify it.

2. The method according to claim 1 further comprising separating the labeled live microorganism from unlabeled microorganisms in the sample.

3. The method according to claim 1, wherein the reactive chemical label and the functional group comprise paired chemical species, the paired chemical species selected from the group consisting of an alkyne/azide pair, a nitrone/alkyne pair, an azide/phosphine pair, an azide/strained alkyne pair, a strained alkene/tetrazine pair, an aldehyde/aminiooxy pair, an aldehyde/hydrazide pair, a ketone/aminooxy pair, a ketone/hydrazide pair, a thiol/alkene pair and an alkene/diaryl tetrazole pair.

4. The method according to claim 1, wherein the functional group of the reporter and/or capture element comprises an azide group.

5. The method according to claim 1, wherein the same reactive chemical label comprises an alkyne group.

6. The method according to claim 1, wherein the reporter and/or capture element is bound to a surface of a physical substrate.

7. The method according to claim 6, wherein the physical substrate comprises a magnetic particle, a magnetic bead or a microfluidic device.

8. The method according to claim 1, wherein each of said one or more biomolecular precursors is specific for the live microorganism.

9. The method according to claim 1, wherein the one or more biomolecular precursors is an amino acid, a nucleic acid, a sugar or a fatty acid, or a mixture of two or more thereof.

10. The method according to claim 9, wherein the one or more biomolecular precursors is a 3-deoxy-D-manno-oct-2-ulosonic acid analogue.

11. The method according to claim 9, wherein the one or more biomolecular precursors is methionine or a methionine analogue.

12. The method according to claim 1, wherein step a) comprises contacting the sample with at least two different biomolecular precursors, each labeled with the same reactive chemical label.

13. The method according to claim 1, wherein the one or more biomolecular precursors comprises a mixture of methionine or a methionine analogue and a 3-deoxy-D-manno-oct-2-ulosonic acid analogue.

14. The method according to claim 1, wherein the microorganism is a species of bacteria.

15. The method according to claim 1, wherein an immobilized strain-specific antibody is used to capture the labeled live microorganism.

16. The method according to claim 15, wherein the strain-specific antibody is immobilized by a magnetic bead.

17. A kit for selectively identifying a live microorganism in a soil, food or water sample comprising:
   a) a biomolecular precursor labeled with a reactive chemical label,
   b) a reporter and/or capture element bearing a functional group that reacts with the reactive chemical label,
   c) a vessel for growing the live microorganism and conducting a reaction between the labeled biomolecular precursor and said reporter and/or capture element bearing a functional group that reacts with the reactive chemical label,
   d) growth medium for the live microorganism,
   e) nutritional factors necessary for growing the live microorganism, and
   f) instructions for using the kit to identify the live microorganism.

18. A method of selectively identifying a live microorganism in a sample comprising:
   a) treating the sample with a medium containing amino acid biosynthesis inhibitory amino acids,
   b) contacting the sample with an amino acid labeled with a reactive chemical label;
   c) growing the live microorganism under conditions that promote selective growth of the live microorganism to permit the live microorganism to utilize the amino acid labeled with the reactive chemical label to synthesize labeled biomolecules on a cell surface of the live microorganism to produce a labeled live microorganism;
   d) contacting the labeled live microorganism with a reporter and/or capture element bearing a functional group that reacts with the reactive chemical label; and,
   e) analyzing the labeled live microorganism to identify it.

19. The method of claim 18, wherein the labeled amino acid labeled with the reactive chemical label is methionine or a methionine analogue.

* * * * *